(12) United States Patent
Barnard et al.

(10) Patent No.: US 6,254,831 B1
(45) Date of Patent: Jul. 3, 2001

(54) OPTICAL SENSORS WITH REFLECTIVE MATERIALS

(75) Inventors: Steven M. Barnard, Framingham; Thomas C. Collins, Milford; Susan L. Cudmore, Upton; Richard W. Mason, Millis; Christiane Munkholm, Salem; Rudolf E. Slovacek, Norfolk; Kevin J. Sullivan, Medfield, all of MA (US)

(73) Assignee: Bayer Corporation, East Walpole, MA (US)

( * ) Notice: Subject to any disclaimer, the term of this patent is extended or adjusted under 35 U.S.C. 154(b) by 0 days.

(21) Appl. No.: 09/009,917

(22) Filed: Jan. 21, 1998

(51) Int. Cl.⁷ .................................................. G01N 21/64
(52) U.S. Cl. ..................................... 422/82.08; 250/458.1
(58) Field of Search ........................... 422/82.07, 82.08; 250/458.1, 459.1

(56) References Cited

U.S. PATENT DOCUMENTS

| | | | |
|---|---|---|---|
| 2,761,417 | 9/1956 | Russell et al. | 118/410 |
| 3,662,802 | 5/1972 | Bedell | 149/36 |
| 3,992,158 | 11/1976 | Przybylowicz et al. | 23/253 |
| 4,003,707 | 1/1977 | Lübbers et al. | 23/232 |
| 4,042,335 | 8/1977 | Clément | 23/253 |
| 4,356,149 | 10/1982 | Kitajima et al. | 422/56 |
| 4,381,921 | 5/1983 | Pierce et al. | 436/535 |
| 4,476,870 | 10/1984 | Peterson et al. | 128/634 |
| 4,587,101 | 5/1986 | Marsoner et al. | 422/56 |
| 4,645,744 | 2/1987 | Charlton et al. | 436/74 |
| 4,649,123 | 3/1987 | Charlton et al. | 436/79 |
| 4,670,218 | 6/1987 | Gantzer et al. | 422/56 |
| 4,680,268 | 7/1987 | Clark, Jr. | 435/291 |
| 4,689,309 | 8/1987 | Jones | 436/95 |
| 4,716,363 | 12/1987 | Dukes et al. | 324/77 |
| 4,734,375 | 3/1988 | Charlton | 436/74 |
| 4,752,115 | 6/1988 | Murray, Jr. et al. | 350/96.29 |
| 4,781,890 | 11/1988 | Arai et al. | 422/56 |
| 4,810,655 | 3/1989 | Khalil et al. | 436/138 |
| 4,824,789 | 4/1989 | Yafuso et al. | 436/68 |
| 4,857,472 | 8/1989 | Wolfbeis | 436/122 |
| 4,861,727 | 8/1989 | Hauenstein et al. | 436/136 |
| 4,895,156 | 1/1990 | Schulze | 128/634 |
| 4,895,704 | 1/1990 | Arai et al. | 422/57 |
| 4,919,891 | 4/1990 | Yafuso et al. | 422/58 |

(List continued on next page.)

FOREIGN PATENT DOCUMENTS

| | | | | |
|---|---|---|---|---|
| 0105870 | 10/1983 | (EP) | | G01N/33/84 |
| 0119861 | 11/1987 | (EP) | | G01N/33/72 |

(List continued on next page.)

OTHER PUBLICATIONS

Aartsma, T. et al., "Porphyrns.43. Triplet Sublevel Emission of Platinum Tetrabenzoporphyrin by Spectrothermal Principal Component Decompostion"; *J. Am. Chem. Soc.* 104, pp. 6278–6283 (1982).

(List continued on next page.)

*Primary Examiner*—Jeffrey Snay
(74) *Attorney, Agent, or Firm*—Reed & Associates

(57) ABSTRACT

Provided is an optical sensor including a support and a detection layer, wherein the detection layer includes:

(a) a luminescent material wherein the luminescence intensity of the luminescent material varies as the amount of an analyte varies;

(b) a reflective material having a highly efficient reflectance of the wavelengths of excitation and of emission of the luminescent material; and (c) a polymeric binder to support and hold together the luminescent material and the reflective material. Such an optical sensor can be advantageously used in the detection of gaseous, ionic, and nonionic analytes in highly scattering samples. Also provided are methods for the manufacture of such optical sensors.

34 Claims, 11 Drawing Sheets

U.S. PATENT DOCUMENTS

| | | | |
|---|---|---|---|
| 4,974,929 | 12/1990 | Curry | 350/96.29 |
| 4,994,396 * | 2/1991 | Lefkowitz et al. | 436/136 |
| 5,030,420 | 7/1991 | Bacon et al. | 422/82.07 |
| 5,043,286 | 8/1991 | Khalil et al. | 436/136 |
| 5,047,350 | 9/1991 | Switalski et al. | 436/136 |
| 5,075,127 | 12/1991 | Yafuso et al. | 427/2 |
| 5,081,041 | 1/1992 | Yafuso et al. | 436/68 |
| 5,081,042 | 1/1992 | Yafuso et al. | 436/68 |
| 5,091,800 | 2/1992 | Offenbacher et al. | 359/350 |
| 5,127,405 | 7/1992 | Alcala et al. | 128/633 |
| 5,173,432 | 12/1992 | Lefkowitz et al. | 436/138 |
| 5,190,729 | 3/1993 | Hauenstein et al. | 422/91 |
| 5,208,147 | 5/1993 | Kagenow et al. | 435/14 |
| 5,250,264 * | 10/1993 | Walt et al. | 422/82.07 |
| 5,260,195 | 11/1993 | Azhar et al. | 435/25 |
| 5,281,825 | 1/1994 | Berndt et al. | 250/458.1 |
| 5,298,144 | 3/1994 | Spokane | 204/403 |
| 5,298,741 * | 3/1994 | Walt et al. | 436/172 |
| 5,310,525 | 5/1994 | Churchouse et al. | 422/56 |
| 5,326,531 | 7/1994 | Hahn et al. | 422/82.06 |
| 5,341,805 | 8/1994 | Stavridi et al. | 128/633 |
| 5,352,348 | 10/1994 | Young et al. | 204/153.12 |
| 5,387,329 | 2/1995 | Foos et al. | 204/415 |
| 5,387,525 | 2/1995 | Munkholm | 436/111 |
| 5,453,248 | 9/1995 | Olstein | 422/82.07 |
| 5,462,858 | 10/1995 | Bale Oenick et al. | 435/16 |
| 5,462,879 | 10/1995 | Bentsen | 436/136 |
| 5,464,777 | 11/1995 | Yip | 436/98 |
| 5,494,562 | 2/1996 | Maley et al. | 204/403 |
| 5,506,148 | 4/1996 | Munkholm | 436/111 |
| 5,520,883 | 5/1996 | Charlton et al. | 422/56 |
| 5,552,272 * | 9/1996 | Bogart | 435/6 |
| 5,601,694 | 2/1997 | Maley et al. | 204/415 |
| 5,605,152 | 2/1997 | Slate et al. | 128/634 |
| 5,624,847 | 4/1997 | Lakowicz et al. | 436/68 |
| 5,631,340 | 5/1997 | Olstein | 528/59 |
| 5,863,460 * | 1/1999 | Slovacek et al. | 422/82.07 |

FOREIGN PATENT DOCUMENTS

| | | | |
|---|---|---|---|
| 0249851 | 12/1987 | (EP) | . |
| 0352610 | 1/1990 | (EP) | . |
| 0409033 | 7/1990 | (EP) | G01N/21/64 |
| 0442276 | 1/1991 | (EP) | A61B/5/00 |
| 0142849 | 8/1992 | (EP) | G01N/33/52 |
| 0287328 | 10/1993 | (EP) | C07D/498/08 |
| 0287327 | 7/1994 | (EP) | C07D/498/08 |
| 87/00023 | 1/1987 | (WO) | A61B/5/00 |
| 90/07107 | 6/1990 | (WO) | G01N/21/64 |
| 92/19957 | 11/1992 | (WO) | G01N/21/76 |
| 95/10522 | 4/1995 | (WO) | C07D/487/22 |
| 95/26501 | 10/1995 | (WO) | G01N/31/22 |
| 95/30148 | 11/1995 | (WO) | C01N/31/22 |
| 97/37210 | 10/1997 | (WO) | G01N/21/64 |

OTHER PUBLICATIONS

Brandrup, J. et al., "Permeability and Diffusion Data" Polymer Handbook, 3rd edition, pp VI/433–VI/449, John Wiley and Sons, New York, NY (1989).

Bruno, et al., "All–Solid–State Miniaturized Fluorescence Sensor Array for the Determination of Critical Gases and Electrolytes in Blood" *Anal. Chem.* 69, pp. 507–513 (1997).

Demas, J. et al., "Design and Applications of Highly Luminescent Transition Metal Complexes"; *Analytical Chemistry*, vol. 63, No. 17; pp. 829–837 (1991).

Kautsky, V. et al., "Nachweis geringster Sauerstoffmengen durch Phosphoreszenztilgung", *Zeitschrift fir anorganische und allgemeine Chemie. Band* 222, pp. 126–134 (1935). (German).

Kautsky, V. et al., "Luminescenzumwandlung durch Sauertoff Nachweis geringster Sauerstoffmengen", *Zeitschrift Naturforschung* 2a, pp. 167–172 (1947). (German).

Klimant, I. et al., "Oxygen–Sensitive Luminescent Materials Based on Silicone–Soluble Ruthenium Diimine Complexes" *Anal. Chem.* 67 pp. 3160–3166 (1995).

Lui, Hsue–Yang et al., "Oxygen Permeability of Sol–Gel Coatings", *Applied Spectroscopy*, vol. 46, No. 8 pp. 1266–1272 (1992).

MacCraith et al., "Optical Chemical Sensors Based on Sol–Gel Materials: Recent Advances and Critical Issues", *J. Sol–Gel Sci. and Tech.*, vol. 8, pp. 1053–1061 (1997).

Papkovsky et al., "Phosphorescent Complexes of Porphyrin Ketones: Optical Properties and Application to Oxygen Sensing", *Anal. Chem.* 67, pp. 4112–4117 (1995).

Papkovsky et al., "Phosphorescent Polymer Films for Optical Oxygen Sensors", *Biosensors & Electronics* 7, pp 199–206 (1991).

Roffey, "Photopolymerization of Surface Coatings", *Wiley-Interscience*, p. 110–117 (1985).

Salame, M. "Transport Properties of Nitrile Polymers", *J. Polymer Sci. Symp.* 41, pp 1–15 (1973).

Stern, V. et al., "Uber die Abklingungszeit der Fluoreszenz", *Physik. Zeitschr.* XX; pp. 183–188 (1919). (German).

Vinogradov et al., "Metallotetrabenzoporphyrins. New Phosphorescence Probes for Oxygen Measurements", *J. Chem. Soc. Perkin Trans.* 2, pp. 103–111 (1995).

Watts, R.J. et al., "Spectroscopic Characterization of Complexes of Ruthenium (II) and Iridium (III) with 4,4'–Dipheynl1–2,2'–bipyridine and 4,7–Diphenyl–1, 10–phenanthroline", *J. Am. Chem. Soc.* 93, pp. 3184–3188 (1971).

Yang et al., "Oxygen Permeability Coefficients of Polymers for Hard and Soft Contact Lens Applications", *J. Membrane Sci.* 9, pp. 53–67 (1981).

* cited by examiner

OPTICAL SENSORS WITH REFLECTIVE MATERIALS

TECHNICAL FIELD

The present invention relates generally to optical sensors and to methods for producing optical sensors. More particularly, the present invention relates to optical sensors based on luminescent detectors which comprise highly reflecting materials in the same layer that contains luminescent materials. This layer of luminescent material and reflecting material typically forms an outer surface of the optical sensor and is in direct contact with the mixture containing the materials to be analyzed.

BACKGROUND

Optical sensors based on fluorescent or phosphorescent materials are known for use in detecting various gases and ionic materials in fluid samples, such as blood and sea water. Typically, oxygen sensors are based on quenching of the luminescence of luminescent materials within the sensors by the analyte gases in a sample. As described in MacCraith et al., *J Sol-Gel Sci. and Tech.*, 8, pages 1053–1061 (1997) and references therein, the variation in the luminescence signal with analyte concentration is described by the Stern-Volmer equation:

$$I_0/I = 1 + K_{sv}[\text{analyte}]$$

where $I_0$ is the luminescence signal in the absence of the analyte and $K_{sv}$ is the Stern-Volmer quenching constant which determines sensitivity. For reliable analyses, it is preferable to achieve a linear relationship or response between the luminescence signal and the amount, such as partial pressure of a gas either in a gaseous or dissolved form.

Alternatively, such optical sensors may employ fluorescent dyes which change their absorbance properties and hence, indirectly alter their emission yield upon protonation or deprotonation according to the sample or internal sensor pH. Two examples of such sensors include a $CO_2$ sensor with the dye hydroxypyrenetrisulfonic acid, as described in U.S. Pat. No. 5,506,148, and a pH sensor with the dye fluorescein, as described in WO 95-30148 to Alder, et al., both of which are incorporated by reference herein.

In these optical sensors, a substrate which is transparent to the excitation and emission wavelengths of the luminescent material is typically used. This type of substrate makes it possible to bring a thin sensor coating or layer containing the luminescent material on the substrate into contact with the sample while permitting the excitation light to reach the sensor coating and the emission signal generated by the luminescent material to be detected through the transparent substrate. In general, with this approach to optical sensors, it is sometimes difficult to achieve reliable analytical measurements because specific samples, such as blood and milk, tend to absorb, or scatter, or reflect the excitation light and the emission signal either back into the sensor detection layer or back into the detection optics through the transparent substrate. Other types of optical interference are stray light from the ambient conditions around the optical sensor and sample and stray light from a second optical sensor located in the vicinity of the first sensor as well as fluorescence from the bulk sample (i.e., bilirubin fluorescence in the case of blood).

One approach to solving this problem has been to place a second coating layer over the sensing or detection layer and thus interpose a separate layer between the sensing layer and the sample. This second coating layer typically absorbs and blocks the excitation light and emission signal to prevent them from reaching the sample. Thus, any sample-induced changes due to hematocrit effects on absorption, scattering, or reflection of the excitation light and emission signal are substantially reduced.

The use of a second layer over the sensing layer has been described for fluorescence based sensors utilizing chemical processes to produce an opaque but permeable second layer which is laminated or coated onto the sensing layer. For example, U.S. Pat. No. 5,091,800 to Offenbacher et al. discloses the use of ion permeable cover membranes made from crosslinked polyvinyl alcohol or cellophane which is stretched on a form and then impregnated with silver, gold, or platinum colloidal particles through a series of chemical treatments to form an opaque membrane. This opaque membrane is then laid in a separate process step over the sensing layer. U.S. Pat. Nos. 4,919,891; 5,075,127; 5,081,041; and 5,081,042 to Yafuso et al. describe other examples of opaque second layers over the sensing layer where the opaque second or cover layer is an ion permeable cover membrane impregnated with a non-reflective opaque material such as carbon black or, alternatively, is a coating of a cellulosic resin with non-reflective opaque materials such as copper phthalocyanine or carbon black.

These sensors do, however, have disadvantages related to requiring an additional layer in their production. The introduction of a second layer between the sample and the detection layer disadvantageously tends to block or inhibit the requisite contact between the analyte and the detection layer. To overcome this drawback, the second layer must be highly permeable to the analyte and adhere well to the detection layer. In addition to the increased expense of a second process step and permeability issues, the variations in material compositions and properties can make this second opaque layer especially problematical when considering material compatibilities between the sensing and opaque layers in production and between the opaque layer and the sample in use.

These extra complexities and disadvantages of a second or cover layer interposed between the sensing layer and the sample are multiplied in the event that two or more different sensing layers are present in a single optical sensor for the detection of two or more different analyzable materials or analytes, such as described in a copending U.S. patent application Ser. No. 09/009,917 entitled "Optical Sensor and Method of Operation," which is fully incorporated herein by reference and referred to hereinafter as the "Chiron Sensor Application," filed on even day herewith by the common assignee. Each of these different sensing layers would require a matched second or cover layer, probably different for each sensing layer. Also, the processing, chemistry, and permeability of the opaque second or cover layer adds complexity and would be more difficult to control on a consistent production basis.

An alternative type of optical sensor is based on differences in absorbance rather than differences in luminescence. These absorbance based sensors typically require the excitation light to be transmitted through the sensing layer after exposure of the layer to the sample being analyzed. The analysis is performed using changes in the transmission or absorbance spectrum of the sensor or, in the case of opaque samples, by using changes in the reflectance spectrum of the sensor. The detection process for absorbance based sensors is generally less complex than for luminescence sensors, for example, because only the absorbance wavelength enters into the analysis. There is no secondary emission wavelength so that complications due to light scattering effects are confined to a single wavelength. However, luminescence sensing is more specific and hence significantly more sensitive due in part to its dependence upon two separate wavelengths (i.e., the excitation and emission) rather than just one wavelength. It therefore operates at much lower analyte levels of detection and with smaller sample volumes than absorption analysis.

One variation of the absorbance based sensors is a multilayer design with a reagent layer where the analyte reacts with a reagent to form a detectable species which diffuses to a detection layer where its amount is measured, as described in U.S. Pat. No. 4,042,335 to Clement. It also contains additional layers, such as a spreading layer, for a total of 3 or more layers in the optical sensor. Typically, this type of optical sensor uses a reflectance based measurement system with a transmitting substrate in a slide frame holder. For the particular measurement requirements of these sensors, a separate light blocking layer containing a reflective opaque material, such as titanium dioxide ($TiO_2$), as one of the multiple layers has been described in U.S. Pat. No. 3,992,158 to Przybylowicz et al. and in U.S. Pat. No. 4,042,335 to Clement; both of which are fully incorporated herein by reference; and in U.S. Pat. Nos. 4,781,890 and 4,895,704 and Eur. Pat. 142,849 B1, all to Arai et al. Alternatively, the opaque materials can be in the spreading layer, as described in U.S. Pat. No. 3,992,158 to Przybylowicz et al. U.S. Pat. No. 4,895,704 to Arai et al. describes the incorporation of light-scattering particulates, such as titanium dioxide, in a hydrophilic layer containing a reagent or containing a registration layer, to make the light transmittance in the range of 2.5 to 10% at the wavelengths used for measuring the detectable species.

It has been suggested by Klimant et al. in Anal Chem. 67, pages 3160–3166 (1995) that one might incorporate $TiO_2$ into a luminescent sensing layer although they were unsuccessful in producing an oxygen sensor which had the required response speed with the opacity to efficiently block optical interference.

SUMMARY OF THE INVENTION

One aspect of the present invention pertains to an optical sensor comprising a support and a detection layer, wherein the detection layer comprises:
(a) a luminescent material wherein the luminescence intensity of the luminescent material varies as the amount of an analyte varies;
(b) a reflective material having a highly efficient reflectance of the wavelengths of excitation and of emission of the luminescent material; and
(c) a polymeric binder to support and hold together the luminescent material and the reflective material.

In one embodiment, the detection layer of the optical sensor of the present invention has a thickness of from 0.2 to 15 microns. In a preferred embodiment, the detection layer has a thickness of from 0.5 to 10 microns. In a more preferred embodiment, the detection layer has a thickness of from 1 to 8 microns.

In one embodiment, the reflective material of this invention is present in the amount of 5 to 65% of the weight of the detection layer. In a preferred embodiment, the reflective material is present in the amount of 10 to 50% of the weight of the detection layer and, more preferably, in the amount of 30 to 50% of the weight of the detection layer.

In one embodiment of this invention, the reflective material is a pigment. Suitable reflective pigments for use in this invention include, but are not limited to, titanium dioxide, zinc oxide, antimony trioxide, barium sulfate, and magnesium oxide. Titanium dioxide or its commercial equivalent is a particularly preferred reflective pigment.

In a preferred embodiment of this invention, the detection layer is an outer layer of the optical sensor adapted for contact with a sample or mixture containing an analyte. In a particularly preferred embodiment of this aspect, the optical sensor consists of a support and a detection layer as a single layer optical sensor.

In one embodiment, the luminescent material is a fluorescent material or combination of materials that produce fluorescence. In another embodiment, the luminescent material is a phosphorescent material. In a preferred embodiment, the luminescent material is platinum octaethyl porphyrin.

In one embodiment, the polymeric binder of the present invention comprises a hydrophobic binder. In a preferred embodiment, the polymeric binder comprises a methacrylate based polymer or copolymer. In a particularly preferred embodiment, the polymeric binder is a copolymer of ethylhexyl methacrylate and methyl methacrylate.

In one embodiment, the support is substantially transparent to the wavelengths of excitation and of emission of the luminescent material. In a preferred embodiment, the support is a transparent flexible plastic film.

In one embodiment, the analyte is a gas. In one embodiment, the analyte gas is oxygen. In one embodiment, the analyte is an ionic material. In another embodiment, the analyte is a nonionic material.

Another aspect of the present invention pertains to methods for preparing an optical sensor comprising the steps of: (a) providing a support; and (b) coating a liquid mixture onto the support and subsequently drying the liquid mixture to form a solid detection layer, as described herein, on one side of the support.

In one embodiment of the methods, the optical sensor comprises two or more detection layers coated in a pattern on the support. In a preferred embodiment of the methods, the two or more detection layers coated in a pattern on the support are capable of sensing the concentration of two or more different analytes. In another embodiment of the methods, the two or more detection layers coated in a pattern on the support are outer layers of the optical sensor adapted for contact with the analyte. In a preferred embodiment of the methods, the two or more detection layers, coated in a pattern on the support as outer layers of the optical sensor, are adapted for contact with two or more different analytes in a sample.

In one embodiment of the methods, the detection layer is heated above the glass transition temperature of the polymeric binder and then cooled back to ambient conditions in a curing process.

DETAILED DESCRIPTION OF THE INVENTION

Figure 1:
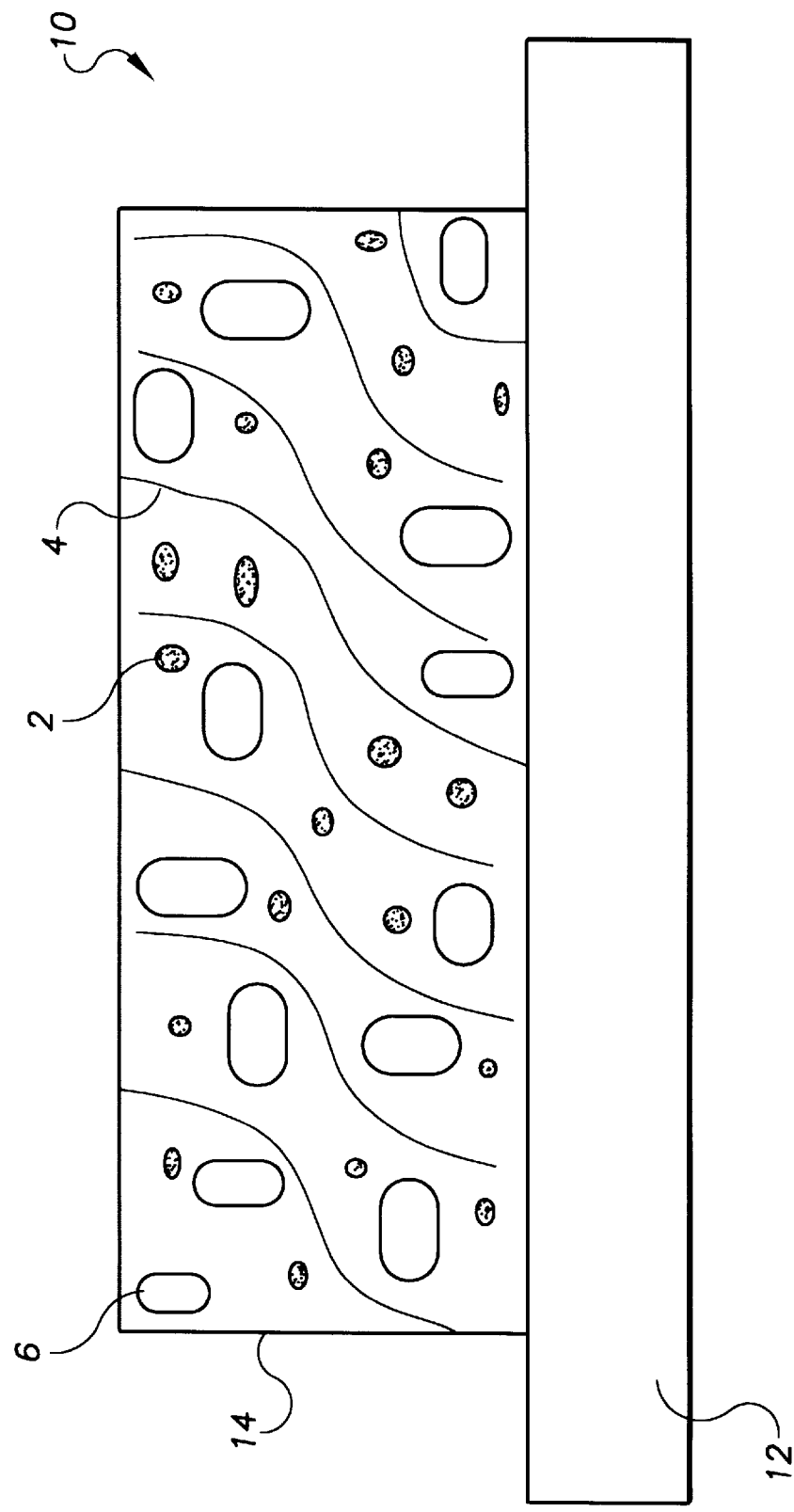
FIG. 1 is a representation of the components to an optical sensor in the present invention.

As illustrated in FIG. 1, the present invention pertains to an optical sensor 10 comprising a support 12 and a detection layer 14, wherein the detection layer comprises:

(a) a luminescent material 2 wherein the luminescence intensity of the luminescent material varies as the amount of an analyte varies;

(b) a reflective material 6 having a highly efficient reflectance of the wavelengths of excitation and of emission of said luminescent material; and, (c) a polymeric binder 4 to support and hold together the luminescent material 2 and the reflective material 6 in a sensing environment accessible to sample analytes In a luminescence based optical sensor 10 for use in measuring the amount of various analyzable materials or analytes in a sample, an excitation wavelength is selected to induce the luminescence. This excitation wavelength is typically chosen based on the absorption spectrum of the luminescent material 2 and considerations for the efficiency and reliability of the excitation light source.

Similarly, an emission wavelength is selected to measure the intensity of the luminescence. This emission wavelength is typically chosen based on the luminescence emission spectrum of the luminescent material 2 and considerations for the efficiency and reliability of the emission detection device.

The word "light", as used herein, means radiation over the wavelength range of the ultraviolet, visible, and infrared regions. For luminescence based optical sensors 10, discrete portions of the visible region between 400 and 750 nm are typically utilized for both the excitation and the emission detection wavelengths. By the word "luminescence", as used herein, is meant light emitted by radiative dissipation from an electronically excited state of a molecule. By the word "fluorescence", as used herein, is meant luminescence between states of identical multiplicity, typically between the lowest excited singlet state and the singlet ground state of the molecule. By the word "phosphorescence", as used herein, is meant luminescence between states of differing multiplicity, typically between the lowest excited triplet state and the singlet ground state.

Figure 2:
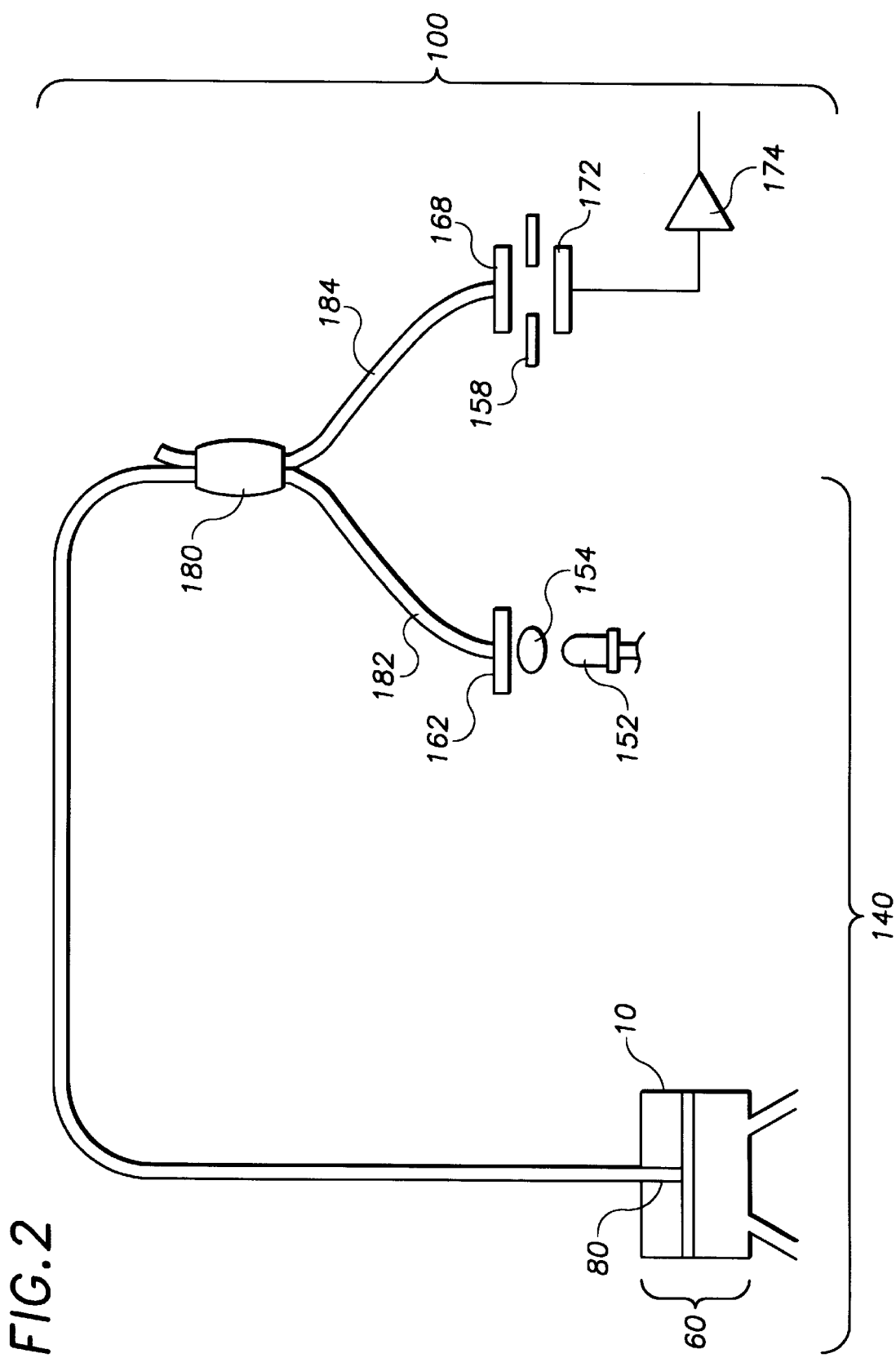
FIG. 2 is a schematic representation of the test apparatus capable of measuring the output signal of a luminescent optical sensor of the present invention.

A suitable device for measuring the response of optical sensors 10 in the present invention is described in FIG. 2. The measurement apparatus 140 is comprised of a flow cell assembly 60 and a source and detector sub-system 100. For the optical source and detector sub-system 100, an LED source 152 and a lens 154 are used to launch excitation light through filter 162 into one leg 182 of the fiber optic splitter 180 (available from American Laubscher Corp., Farmingdale, N.Y., and having a numerical aperture of 0.485). The luminescent light signal returning from the sensor 10 down fiber cable 80 and leg 184 is passed through filter 168 and aperture 158 before detection by a photodiode 172 (available from Hamamatsu Corporation, Bridgewater, N.J.). The output current of emission detector 172 is amplified with a preamplifier 174, such as a Stanford Research SR570 current preamplifier (available from Stanford Research Systems, Inc., Sunnyvale, Calif.), converted to a voltage and recorded for use in analysis. For the case with a pH sensing dye fluorescein used in the detection layer 14 of the optical sensor 10, as described in Example 5, a Panasonic® Blue LED (P389ND available from Digi-Key, Thief River Falls, Minn.) was used for source 152. A 485 nm center wavelength 22 nm half bandwidth filter (available from Omega Optical, Brattleboro, Vt.) was used for filter 162 and a 535 nm center wavelength 35 nm half bandwidth filter (also available from Omega Optical, Brattleboro, Vt.) was used for filter 168. It should be evident that each individual sensor detection layer 14, employing a different dye as the luminescent material 2, will require its own preferred LED source 152, excitation interference filter 162, and emission interference filter 168.

When the luminescence detection layer 14 of optical sensor 10 is brought in contact with the sample by means of flow cell assembly 60 in order to measure the analyte, the optical emission signal that is generated and subsequently conveyed by fiber optic 80 to the excitation and detection sub-system 100 needs to be correlatable to the amount of the analyte which is present. During this measurement, a number of optical interferences may occur between the sample and the excitation and emission light. These interferences may include: absorption of either excitation or emitted light which reaches the sample layer; a scattering, or reflection of the excitation light, which has passed through the sensor 10 or detection layer 14 into the sample, back into the detection layer 14; and a scattering, or reflection of the emission light, which has been emitted from the detection layer 14 into the sample, back through the detection layer 14 and support 12 and subsequently into the emission detection optics. These interferences may combine to significantly alter the emission signal depending on the nature of the sample. Typically, these interferences are not as large as a factor of four, but they still introduce a significant uncertainty in the measurement of the analytes. Another type of optical interference is stray light from the ambient conditions around the optical sensor 10 and sample as they reside in the flow cell assembly 60 during the measurement period or from a second detection layer 14 located near to the first detection layer 14 on a sensor.

To overcome these optical interferences without affecting significantly the interaction between the analyte and the luminescent material, the present invention includes a reflective material 6 added to the luminescent material 2 in the detection layer 14. This reflective material 6 provides a highly efficient reflectance of the wavelengths of excitation and of emission of the luminescent material. Suitable reflective materials are pigments and blushed or voided polymers; and combinations thereof. Blushed or voided polymers as reflective materials are described, for example, in the aforementioned U.S. Pat. No. 3,992,158 to Przybylowicz et al. and 4,042,335 to Clement. Suitable reflective pigments include, but are not limited to, inorganic pigments such as, for example, titanium dioxide, zinc oxide, antimony oxide, magnesium oxide, barium sulfate, and aluminum oxide. Particularly preferred reflective pigments are titanium dioxides, either in their rutile, anatase, or brookite forms, and blushed or voided polymer pigments. Blushed or voided polymers in a pigment form are typically white in appearance, obtain their highly efficient reflectance from light scattering by microscopic voids in the solid polymer, and have little or no solubility in organic solvents or water, These properties also make them compatible with coating mixtures used to apply the detection layer to a support. An example of such a commercially available product is "PERGOPAK®M2" obtainable from MARTINSWERK GmbH, Berkheim, Switzerland. The term "highly efficient reflectance", as used herein, refers to a material having greater than 75% reflection of the wavelength of light, relative to 100% reflectance for magnesium oxide, as measured according to Roffey in Photopolymerization of Surface Coatings, Wiley-Interscience, 1985, pages 110 to 117 and references therein, all of which are fully incorporated herein by reference.

This highly efficient reflectance of the reflective material 6 serves the function of acting as an internal light barrier in the detection layer 14 to reduce optical interaction with the sample in contact with the sensor 10 or detection layer 14. The addition of the reflective material 6 also enhances the emission signal by reflecting excitation light, which may otherwise escape by transmittance into the sample, back into the luminescent material 2 as well as reflecting the luminescent emission back through the support 12 and towards the detector optics in 100. This enhancement of the emission signal by the reflective material 6 is an especially important feature of this invention and is consistent with the benefit of adding a reflective material 6, rather than a non-reflective absorptive material, to a thin detection layer 14. A reflective material 6 blocks light from reaching the sample, as an absorptive material may also do; but the reflective material 6 has the important additional feature of reflecting light to enhance the emission signal which is not available from a non-reflective absorptive material.

It is preferable that the percent reflection of the wavelengths of the excitation and emission of the luminescence based optical sensor 10 by the highly efficient reflective material 6 be relatively high. Preferred are reflective materials with greater than 90% reflection, as measured according to the references cited herein, of the wavelengths of light of interest for the optical sensor. Particularly preferred are reflective materials with greater than 98% reflection.

The particle size of the reflective pigments of the present invention can affect the uniformity of the luminescence response, particularly large particles with average diameters greater than 5 microns when used in thin detection layers with thicknesses of 5 microns or less. Suitable particle sizes for the reflective pigments have an average diameter in the range of 0.05 to 5 microns. Preferred are particle sizes with average diameters in the range of 0.1 to 0.5 microns. A useful form of $TiO_2$ is Ti-Pure® and is available from EI du Pont de Nemours, Wilmington, Del. in several dry grades as well as slurries. $TiO_2$ pigment is also available from Kronos Inc., Houston, Tex., in various grades.

The amount of the reflective material 6 used should be sufficient to reduce the optical interferences from the sample and from stray light to acceptable levels where a sufficient correlation between luminescence intensity and the amount of the analyte is achieved in the sensor measurement system, independent of whether clear aqueous samples or highly turbid blood samples are being used. The specific amount of the reflective material 6 varies depending, for example, on the luminescence properties of the specific luminescent material 2 and polymer binder 4 being used, the final thickness of the sensing layer and the degree of optical interference which must be removed. For example, to reduce by 50% an optical interference originating with the sample, the coating should have a measured absorbance or optical density (O.D.) value of about 2 at the wavelength of interest when the sensor excitation and emission collection optics have a numerical aperture of 0.485. Also, for example, to reduce by 90% an optical interference originating with the sample, the coating should have a measured absorbance or optical density value of about 4 at the wavelength of interest when the excitation and emission optics have a numerical aperture of 0.485. For a thin detection layer 14 this will require a materially higher percentage of the reflective pigment 6 than for a thicker detection layer 14. Suitable weight percentages of the reflective material 6 in the detection layer 14 are in the range of 5 to 65% of the weight of the detection layer as these do not unduly alter the coating solutions enough to prevent their application by standard coating technologies or alter the desired combination of luminescence sensitivity and quantitative response and very rapid response times to the analyte in the sample. Preferably, the weight percentages of the reflective material 6 of the weight of the detection layer 14 are 10 to 50% and, more preferably, are 30% to 50%. Although larger percentages are possible, care must be excercised not to greatly compromise or lose the polymeric binder 4 properties which support and hold together the luminescent material 2 in a specific or desired sensing environment or to interfere with the coating rheology.

The presence of the reflective material 6 in the detection layer 14 of the luminescence based optical sensor 10 eliminates the need for any additional coating layers over the detection layer 14. In a preferred embodiment, the detection layer 14 is an outer layer of the optical sensor 10 adapted for contact with a sample or mixture containing an analyte and is thus applied on the sample side of the optical sensor. In a particularly preferred embodiment, the detection layer 14 is the only layer present on the support 12 of the optical sensor 10.

Many luminescent materials 2 which are useful to provide a concentration variable emission signal in response to gaseous, ionic, and nonionic analytes are conventional and well known in the art and can be used in the present invention. In one embodiment, the luminescent material of this invention is a fluorescent material. Suitable fluorescent materials include, but are not limited to, dyes from the fluorescein, acridine, rhodamine and pyrene families. In one embodiment of this invention, the fluorescent dye used for sensing pH is fluorescein. In another embodiment, the fluorescent dye used for sensing pH changes caused by the presence of carbon dioxide gas is hydroxypyrenetrisulfonic acid.

In another separate embodiment, the luminescent material of this invention is a phosphorescent material. For example, in a preferred embodiment, a phosphorescent material is utilized to measure oxygen gas. Suitable phosphorescent materials include dyes from the porphryin series. In a preferred embodiment, the phosphorescent material is platinum octaethyl porphyrin.

The amount of luminescent material 2 should be sufficient to provide an analyte concentration dependent emission signal which is of sufficient intensity for use in the particular sensor measurement system being used. The specific amount of the luminescent material 2 in the detection layer 14 varies depending, for example, on the quantum yield properties of the specific luminescent material 2 being used, the analyte being measured, and on the other components of the sensor measurement system being used. In general, luminescent dye materials comprise a small fraction of the overall detection layer 14 composition. Typically this ranges from between 0.01 to 3% by weight.

The thickness of the luminescent detection layer 14 can vary for a variety of reasons such as, for example, due to the specific rheology of the polymer component in the solvent matrix and the deposition method used. Suitable detection layer 14 thicknesses are in the range of 0.2 to 15 microns. Preferably, the detection layer 14 thickness is in the range of 0.5 to 10 microns as this serves to promote more rapid response rates. More preferably, the detection layer 14 has a thickness in the range of 1 to 8 microns. Unlike potentiometric electrochemical sensors which rely on potentials established across thick or thin membranes, the optical sensor 10 relies on a bulk equilibration phenomena to expose all the luminescent material (both exposed and buried) to the sample environment.

Suitable distributions of the luminescent material 2 and the reflective material 6 in the detection layer 14 include substantially uniform distributions, such as may be obtained in conventional milling processes, as well as substantially non-uniform distributions as, for example, from adsorption of the luminescent material on the surface of the reflective material or from chemical bonding of the luminescent material to the surface of the reflective material. The luminescent material 2 and the reflective material 6 are preferably both substantially uniformly distributed in the detection layer 14. This may be confirmed by a combination of both conventional visible light microscopy and fluorescent microscopy to identify regions of non-uniform brightness.

In the interaction between the optical sensor 10 and the sample, the permeability of the detection layer 14 to the analyte in the sample and the environment afforded to the luminescent material 2 are essential parameters to control for rapid and reproducible measurements. It is sometimes useful to add additional materials to the detection layer 14 to improve the permeability properties as well as to provide increased mechanical integrity and stability to the detection layer and increased adhesion of the detection layer to the support, especially during contact with the sample containing the analyte and during the measurement period. However, this can somtimes be avoided by careful selection initially of the polymeric binder 4 to have the specific properties desired. Homopolymers, copolymers, terpolymers and more complex polymers may be formulated from the groups consisting of poly(amides), poly(acrylamides), poly(styrenes), poly(acrylates), poly(alkylacrylates), poly(nitriles), poly(vinyl chlorides), poly(vinyl alcohols), poly(dienes), poly(esters), poly(carbonates), poly(siloxanes), poly(urethanes), poly(olefins), poly(imides), and hetero polymeric combinations thereof; cellulosics and derivatives thereof, to have the specific properties desired. Examples of such polymers and the methods for making them may be found in U.S. Pat. No. 5,387,329, which is incorporated herein by reference. The detection layer 14 is preferably insoluble in the fluid sample being measured.

For example, in an embodiment for an oxygen sensor, the detection layer 14 comprises a hydrophobic binder. Although many analytes such as pH or hydrogen ions are in water-based samples or mixtures and would benefit with the addition of a hydrophilic polymeric binder to the detection layer for rapid wetting of the sample into the optical sensor, the requirements for the oxygen sensor favor a different type of polymeric binder 4. In this particular embodiment, the polymeric binder comprises a hydrophobic binder. Suitable hydrophobic binders include, but are not limited to, polymeric materials such as poly(styrenes), poly(esters), poly(olefins), poly(acrylates), poly(alkylacrylates), poly(nitriles), poly(vinyl chlorides), poly(dienes), poly(carbonates), poly(siloxanes), poly(urethanes); and hetero polymeric combinations thereof. In a preferred embodiment, the hydrophobic polymeric binder comprises a methacrylate polymer or copolymer. In a particularly preferred embodiment, the hydrophobic polymer binder is a copolymer of ethylhexylmethacrylate and methylmethacrylate.

In order for the excitation wavelength to effectively enter the detection layer 14 and for the emission signal to travel from the detection layer 14 and travel through the support 12 in order to reach the detection optics, it is important that there is minimal interference from the support 12 itself. Typically, the support 12 is substantially transparent to the wavelengths of excitation and of emission of the luminescent material 2. In a typical use, for example when the luminescent material 2 is platinum octaethyl porphyrin, a typical excitation wavelength is 535 nm and a typical emission wavelength for signal detection is 650 nm. The specific wavelengths of excitation and emission for each optical sensor 10 in the measurement system 140 are the actual wavelengths to which the support 12 needs to be substantially transparent. Suitable supports 12 include, but are not limited to, flexible plastic films, glass plates, and glass and plastics in the form of optical fibers and wave guides. In a preferred embodiment, the support 12 is a flexible plastic film which is substantially transparent to the wavelengths of excitation and of emission of the luminescent material 2. Suitable plastic films include, but are not limited to, polyester such as polyethylene terephthalate, for example as sold under the trademark of MYLAR® by E.I. DuPont de Nemours (Dupont) and as described in the Chiron Sensor Application. Also useable for support 12 are glass microscope slides, ACLAR®(a trademark for poly[trichlorofluoroethylene] plastic films available from Allied-Signal, Inc., Morristown, N.J.), and SARAN® (a trademark for poly[vinylidene chloride] plastic films available from Dow Brands L.P., Midland, Mich.) materials.

The present invention is adapted to the measurement of various analytes. In one embodiment, the analyte is a gas, such as oxygen. In another embodiment, the analyte is the gas, carbon dioxide. While in yet a third embodiment, the analyte is an ionic material and in particular hydrogen ions. Other suitable ionic materials for measurement include, but are not limited to, hydroxyl ions, sodium ions, potassium ions, calcium ions, lithium ions, and either the acidic or basic charged forms of small metabolite molecules such as lactate, creatinine and urea found in aqueous sample environments.

Another aspect of the present invention pertains to the method for preparing an optical sensor comprising: (a) providing a support; and (b) coating a detection layer, as described herein, on one side of the support.

It is often desirable to measure different analytes using a single support 12 for multiple detection layers 14 of the optical sensor 10. In one embodiment of the methods for preparing an optical sensor, the optical sensor 10 comprises two or more detection layers 14 coated in a pattern on the support 12. Typically, this pattern is parallel stripes or parallel coatings with narrow widths on a single support 12. In a preferred embodiment of the methods, the two or more detection layers 14 coated in a pattern on the support are capable of sensing the concentration of two or more different analytes.

It is desirable to have only a single coating process to control in fabricating the optical sensor 10, especially if different detection layers 14 are to be coated on a single support 12. In one embodiment of the methods for preparing an optical sensor, the two or more detection layers 14 coated in a pattern on the support are outer layers of the optical sensor 10 adapted for contact with the analyte. In a preferred embodiment of the methods, the two or more detection layers 14 coated in a pattern on the support 12 as outer layers of the optical sensor 10 are adapted for contact with two or more different analytes.

In order to provide a more consistent binder property such as permeability to the detection layer 14, it may be desirable to remove residual stresses from the layer that may have developed during the fabrication processes. In one embodiment of the methods for preparing an optical sensor, the detection layer, comprising a polymeric binder, is heated above the glass transition temperature of the polymeric binder and then cooled back to ambient conditions. By the term "ambient conditions", as used herein, is meant the temperature and humidity range typical of the office or work environment. This process is commonly refered to a polymer curing and may include other alternative steps.

The following examples illustrate the invention. It is understood, however, that these examples are not to be interpreted as limiting the scope of the invention.

EXAMPLES

Comparative Example 1

Approximately 1 g of a methacrylate copolymer (made from the monomers: ethylhexylmethacrylate and methylmethacrylate in the mole ratio of 1:9) and 20 mg of platinum octaethyl porphyrin (OEP) were dissolved in 2 g of chloroform and spin coated onto glass coverslips. The coated sensors were then placed in a vacuum oven, heated to 105° C. for 1 hour, and then gradually allowed to cool to room temperature overnight. The spin coated detection layer thickness was in the range of 0.5 to 1.0 microns. The magnitude of the sensor luminescent response to tonometered liquid samples was measured as a light signal amplitude change, as described in copending U.S. patent application Ser. No. 08/617,714, to common assignee and incorporated herein by reference.

Figure 3:
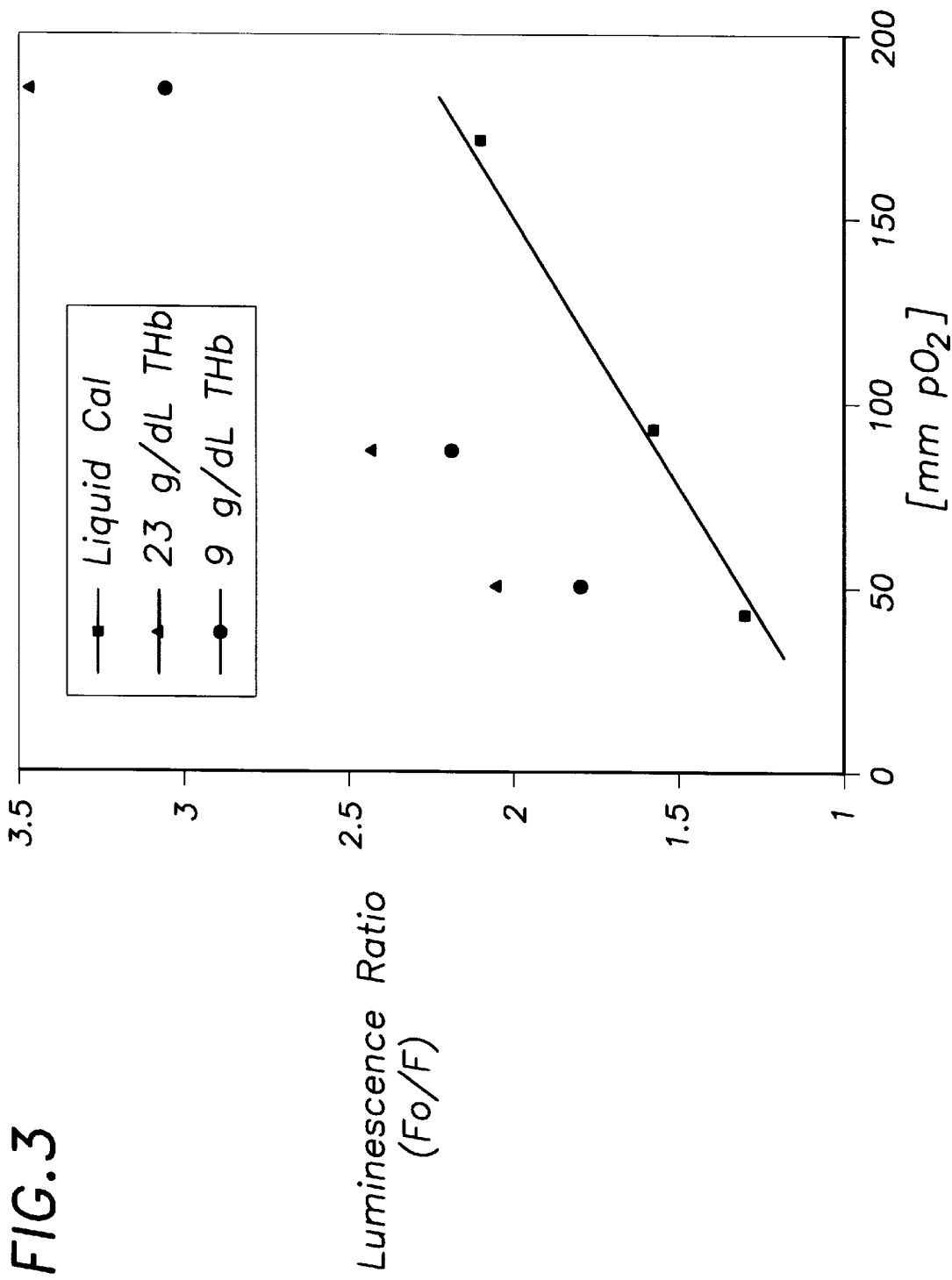
FIG. 3 is a Stern-Volmer plot of the luminescence intensity ratio ($F_0/F$) versus amount of oxygen (mm $pO_2$) for an oxygen sensor, as described in Comparative Example 1, with a clear aqueous buffer calibration sample and with two opaque blood samples having two different concentrations of total hemoglobin (THb).

FIG. 3 shows a Stern-Volmer plot of the luminous intensity ratio ($F_0/F$) versus varying levels of oxygen. When a clear liquid standard calibration solution is measured, the Stern-Volmer plot gives a linear response of the luminescent intensity ratio to varying levels of oxygen. However, when opaque blood samples are measured, and the $F_0$ value determined with a clear liquid standard solution containing no oxygen is used, the response curves are increasingly displaced depending upon the total hemoglobin (THb) in the sample.

Example 1

Figure 4:
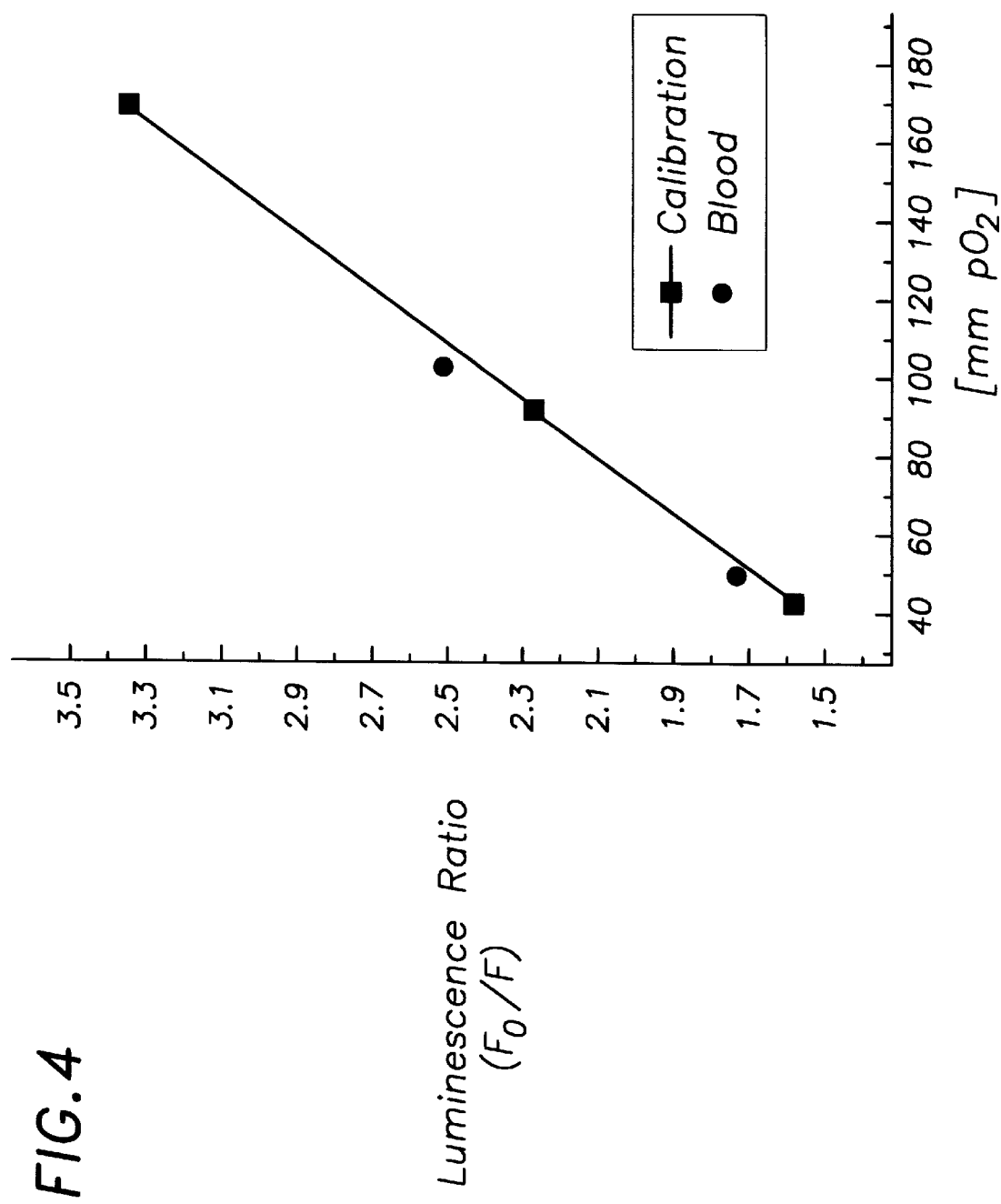
FIG. 4 is a Stern-Volmer plot of the luminescence intensity ratio versus amount of oxygen for an oxygen sensor containing titanium dioxide, as described in Example 1, for both blood and tonometered buffer samples.

Approximately 1 g of ethylhexylmethacrylate and methylmethacrylate copolymer (as described in Comparative Example 1), 1 g of titanium dioxide ($TiO_2$, available from DuPont as Ti-Pure® dry grade R-700), 10 ml of tetrahydrofuran (THF), and 10 tungsten carbide beads were added to a glass jar, capped and milled overnight. 6 mg of OEP was added to 3 ml of the milled mixture and stirred vigorously by vortex mixing. Detection layers from the resulting dye mixture with titanium dioxide were applied to a MYLAR® polyester film support using the deposition procedures described in the Chiron Sensor Application entitled "Optical Sensor and Method of Operation," which was incorporated herein by reference earlier, to provide a dry thickness of about 8 microns. The sensors were then placed in a vacuum oven, heated to 105° C. for 1 hour, and then gradually allowed to cool to room temperature overnight. The results of FIG. 4 show that, in contrast to FIG. 3, tonometered blood samples give a luminescence response ($F_0/F$) matching the Stern-Volmer relation derived for the clear liquid calibration solutions when optical sensors containing $TiO_2$ in the detection layer are used. The points represent the averages of three separate sample measurements of either blood or the liquid standard solutions at each individual point.

Comparative Example 2

Figure 5:
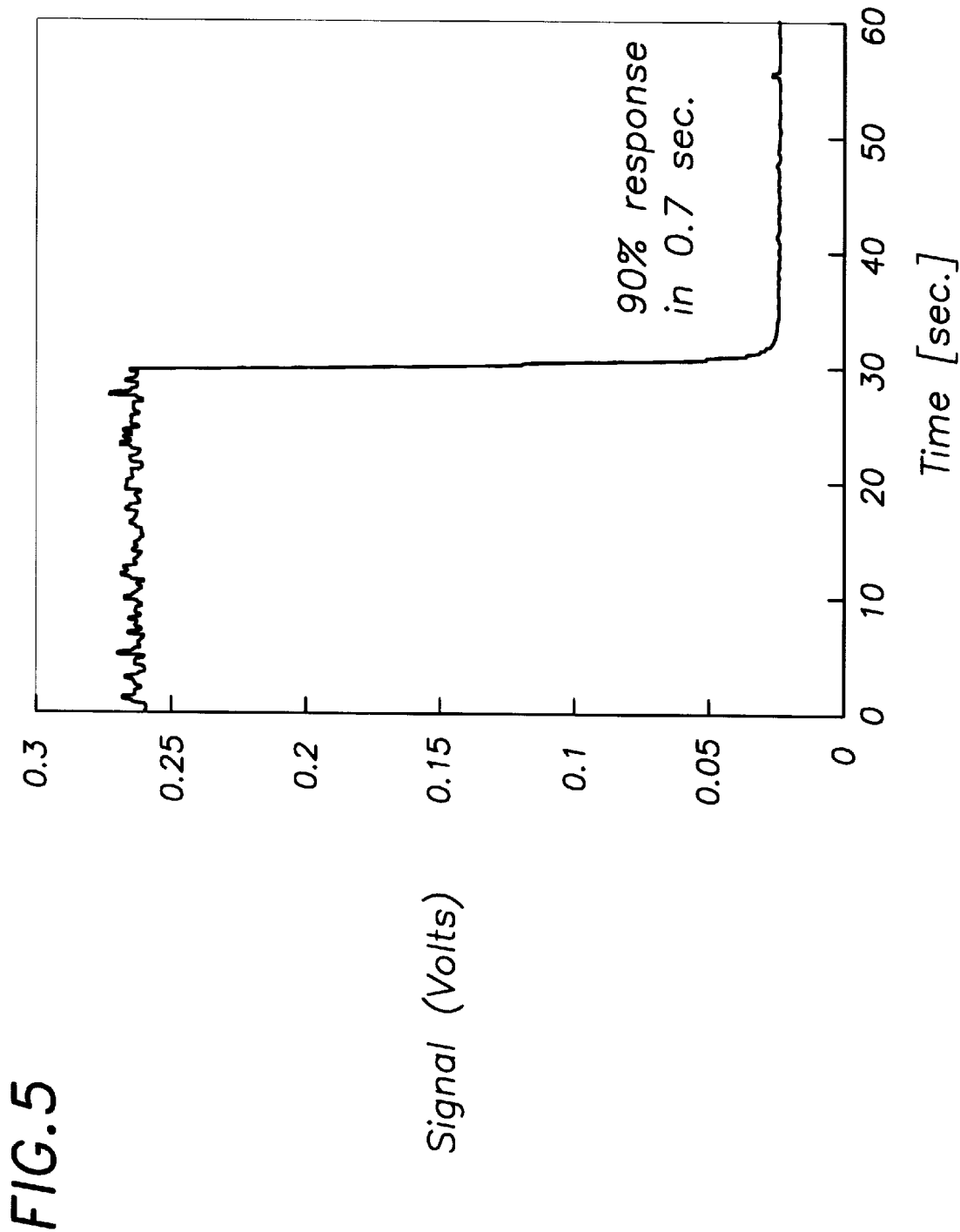
FIG. 5 shows the response speed for achievement of 90% of the final luminescent emission for the control oxygen sensor containing no titanium dioxide, as described in Comparative Example 2.

A comparative control solution without added $TiO_2$ was made by adding 6 mg of OEP, 300 mg of the methacrylate copolymer (as described in Comparative Example 1), and 3 ml of THF to a glass scintillation vial and allowing the resulting mixture to dissolve overnight. Detection layers were fabricated on a MYLAR® polyester film substrate as in Example 1 to provide a dry thickness of about 4 microns and were subsequently heated to 105° C. for 1 hour and then cooled, as described earlier. In contrast to FIG. 4, these control sensors exhibited a substantial error induced by blood samples after calibration with simple aqueous solutions. Other physical properties are described for the control material in FIG. 5 and Table 1. In FIG. 5, the response to a step change in oxygen level by the control sensors was found to be 90% complete by about 0.7 seconds.

Example 2

Figure 6:
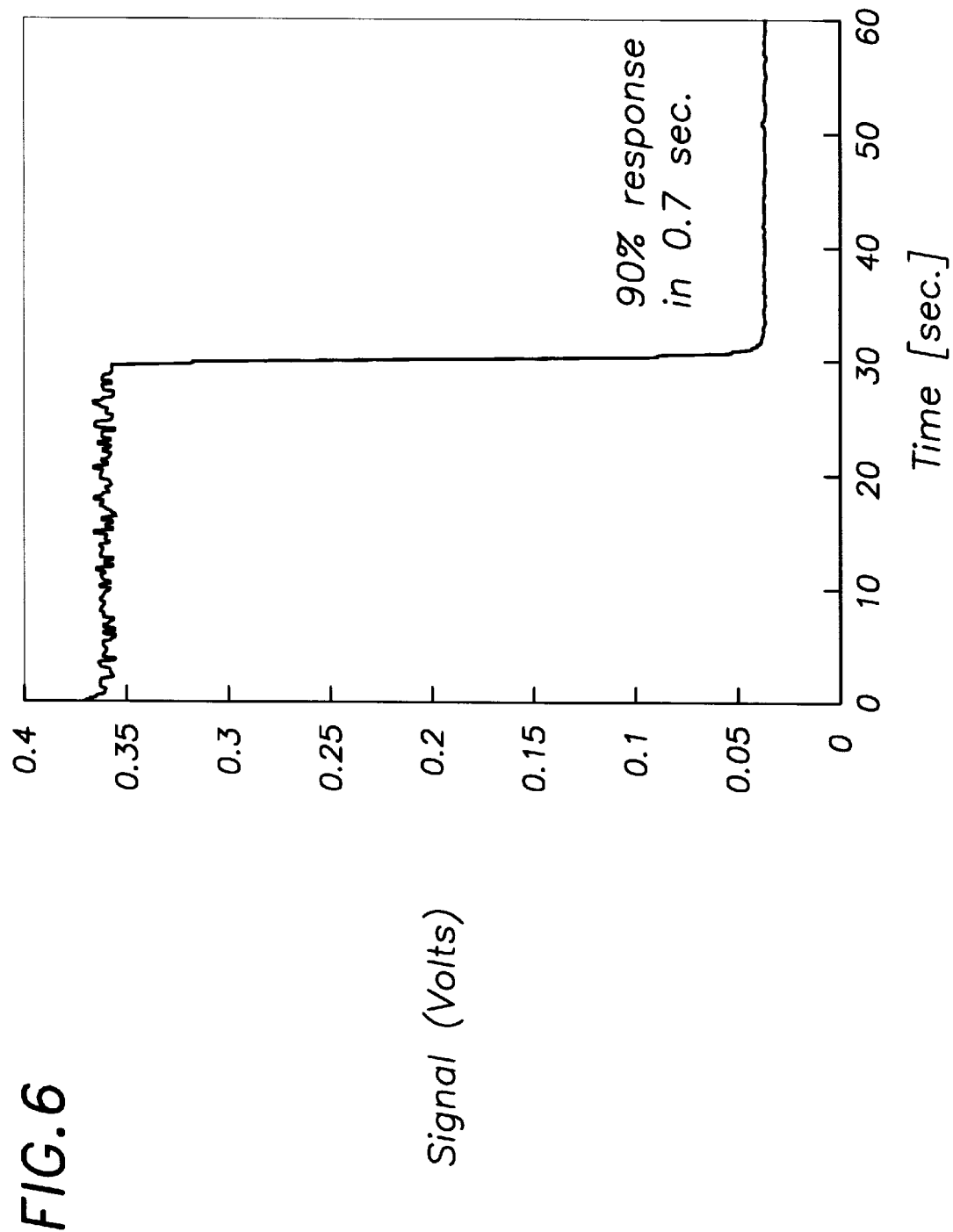
FIG. 6 shows the response speed for achievement of 90% of the final luminescent emission for an oxygen sensor of the present invention containing 50% titanium dioxide, as described in Example 2.

To construct detection layers with varying amounts of $TiO_2$, two initial mixtures A and B were made with the same identical dye, polymer and solvent ratios except that mixture B also contained 50% by weight $TiO_2$ of the combined polymer and $TiO_2$ weight. Mixture A (identical to the control in Comparative Example 2) was made by adding 6 mg of OEP, 300 mg of the methacrylate copolymer (as described in Comparative Example 1), and 3 ml of THF to a glass scintillation vial and allowing the resulting mixture to dissolve overnight. A second mixture was made by adding 1 g of the methacrylate copolymer (as described in Comparative Example 1), 1 g of Ti-Pure® R-700 $TiO_2$, 10 ml of THF and 10 tungsten mixing beads to a glass jar, capping it and milling on a roller apparatus overnight. In a second step, 6 mg of the dye (OEP) was added to and dissolved by vortexing in 3 ml of the second mixture to become mixture B. By mixing solutions A and B in the ratios of 1:0, 3:1, 1:1, 1:3 and 0:1 followed by deposition of the detection layers on a MYLAR® polyester film support, sensors corresponding to 0%, 12.5%, 25%, 37.5% and 50% by weight of $TiO_2$ were fabricated having thicknesses in the range of 4 to 8 microns. The sensors were then placed in a vacuum oven, heated to 105° C. for 1 hour, and then gradually allowed to cool to room temperature overnight. The response to a step change in oxygen level by the 50% $TiO_2$ sensor was found to be 90% complete by about 0.7 seconds as illustrated in FIG. 6.

This was found to compare favorably with the control sensor having no $TiO_2$ as shown earlier in FIG. 5. Thus the response speed of the optical sensors was not significantly affected by the addition of $TiO_2$ to the detection layer.

Several additional properties of the sensors are compared in Table 1. Optical density (O.D.) was determined by the transmittance of light through a detection layer at the wavelength indicated on a Perkin Elmer Model 559 UV/VIS Spectrometer (Norwalk, Conn.). The relative signal amplitude for all sensors was determined after normalization for a constant preamplifier gain and for the standard condition of 21% oxygen at 25° C. The Stern-Volmer constants were determined by exposure of the individual sensors to a series of tonometered aqueous buffer samples.

TABLE 1

| Stripe | % TiO2 | O.D._500 nm | Relative Signal | $K_{SV} \times 10^3$ |
| --- | --- | --- | --- | --- |
| A | 0 | 0.1 | 1.0 | 11.3 |
| B | 12.5 | 1.8 | 2.6 | 11.3 |
| C | 25 | 2.9 | 2.7 | 10.8 |
| D | 37.5 | ~3.0 | 3.1 | 10.4 |
| E | 50 | ~4.0 | 3.1 | 9.6 |

As seen in Table 1, the oxygen sensors coated with $TiO_2$ were found to have slightly lower $K_{sv}$ values than the control sensors without $TiO_2$. This effect was only observable at the higher levels of $TiO_2$. Advantageously, this indicates that the $TiO_2$ at the levels used here has only a small effect on the overall permeability of the sensor or detection layer. It was also observed from the normalized signal amplitudes that reflection by the $TiO_2$ particles has a net positive effect in increasing the sensed signal as well as maintaining the linear response and the luminescence quenching sensitivity, as shown by the $K_{sv}$ values. These advantageous results are surprising in view of the expectation that incorporating reflective materials, such as titanium dioxide particles, internally into a luminescence detection layer would both lower the luminescence output significantly and interfere with the uniformity and consistency of the luminescence quenching results, due to light blocking and light scattering.

Example 3

Figure 7:
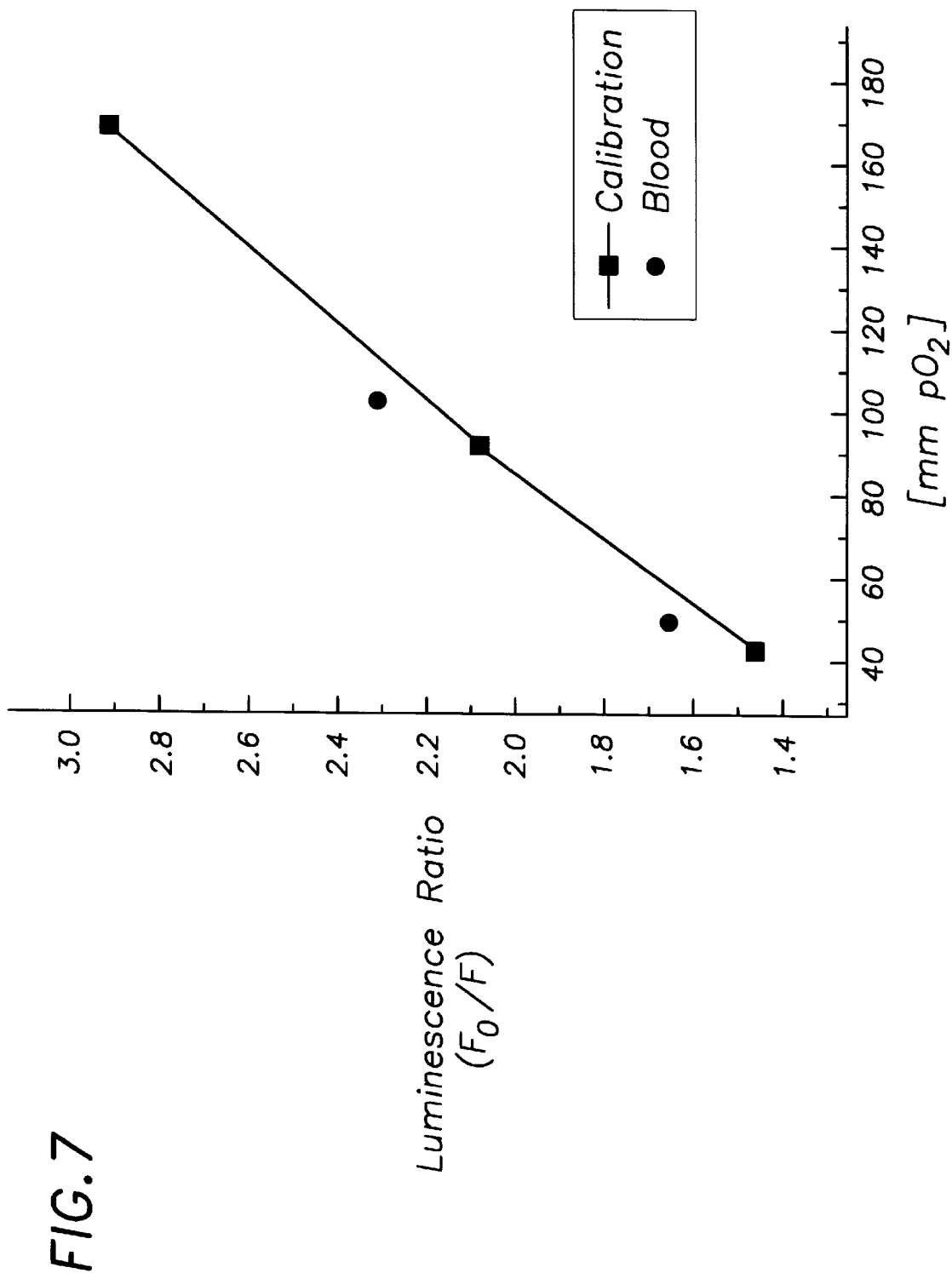
FIG. 7 is a Stern-Volmer plot of the luminescence intensity ratio versus amount of oxygen for an oxygen sensor containing a blush polymer, as described in Example 3, for both blood and tonometered buffer samples.

A first solution was prepared by adding 300 mg of the methacrylate copolymer (as described in Comparative Example 1), 300 mg of the white or blush polymer pigment sold under the trademark of "PERGOPAK® M2" (available from MARTINSWERK GmbH, Berkheim, Switzerland) and 3 ml of THF to a glass scintillation vial and milling the resulting mixture with the aid of tungsten carbide beads overnight. 2 mg of the luminescent oxygen sensing dye (OEP) was added to 1 ml of the milled mixture and vortexed to dissolve the dye. Striped sensor layers were formed on a MYLAR® polyester film support as described in Example 1 and cured by heat treatment to 105° C. for one hour. Measurements of the optical response were performed as in Comparative Example 1. Similar to the case with $TiO_2$ in Example 1, the blood values as shown in FIG. 7, are not significantly distorted but rather appear to follow the Stern-Volmer behavior derived from liquid calibrants. Thus, a blush polymer, in the form of the polymer pigment "PERGOPAK® M2", was used as an alternative reflective material to the $TiO_2$ in reducing the blood scattering effects.

Example 4

Figure 8:
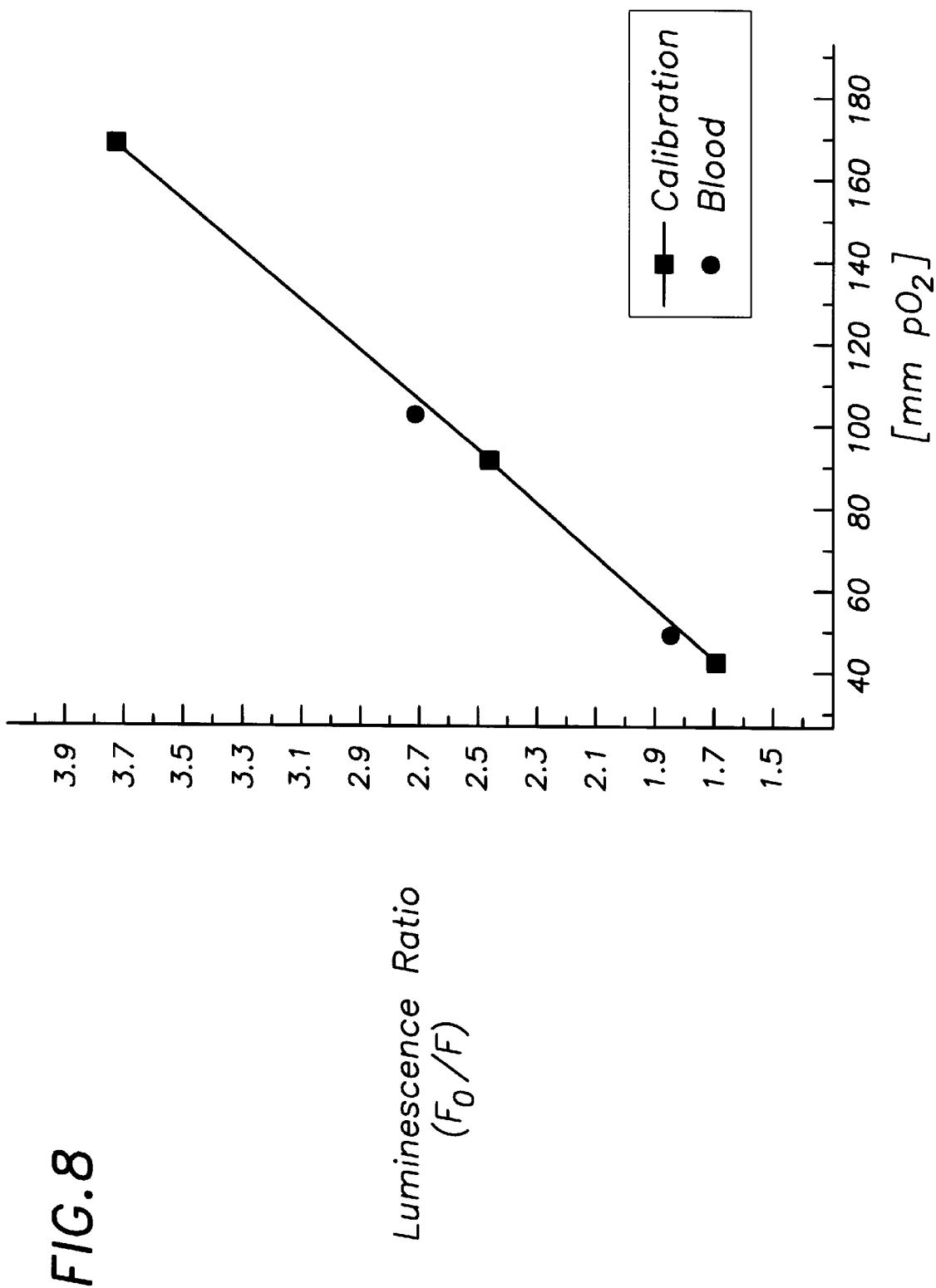
FIG. 8 is a Stern-Volmer plot of the luminescence intensity ratio versus amount of oxygen for an oxygen sensor containing a combination of a blush polymer and titanium dioxide, as described in Example 4, for both blood and tonometered buffer samples.

A first solution was prepared by adding 300 mg of the methacrylate copolymer (as described in Comparative Example 1), 150 mg of the white polymer pigment "PERGOPAK® M2" (available from MARTINSWERK GmbH, Berkheim, Switzerland), 150 mg of Ti-Pure® R-700 $TiO_2$ and 3 ml of THF to a glass scintillation vial and milling the resulting mixture with the aid of tungsten carbide beads overnight. 2 mg of the luminescent oxygen sensing dye (OEP) was added to 1 ml of the milled mixture and vortexed to dissolve the dye. Striped sensor layers were formed on a MYLAR® polyester film support as described in Example 1 and cured by heat treatment to 105° C. for one hour. Measurements of the optical response were performed as in Comparative Example 1. The Stern-Volmer response to tonometered liquid calibrants is plotted in FIG. 8 along with the response to tonometered blood samples. Similar to the case with titanium dioxide in Example 1, and with the "PERGOPAK® M2" alone in Example 3, the blood values in FIG. 8 are not significantly distorted but rather follow the Stern-Volmer behavior even when the $F_0$ value derived from liquid calibrants is used. A combination of the polymer pigment "PERGOPAK® M2" and $TiO_2$ pigment was thus used to reduce the blood scattering effects.

Comparative Example 3

Figure 9:
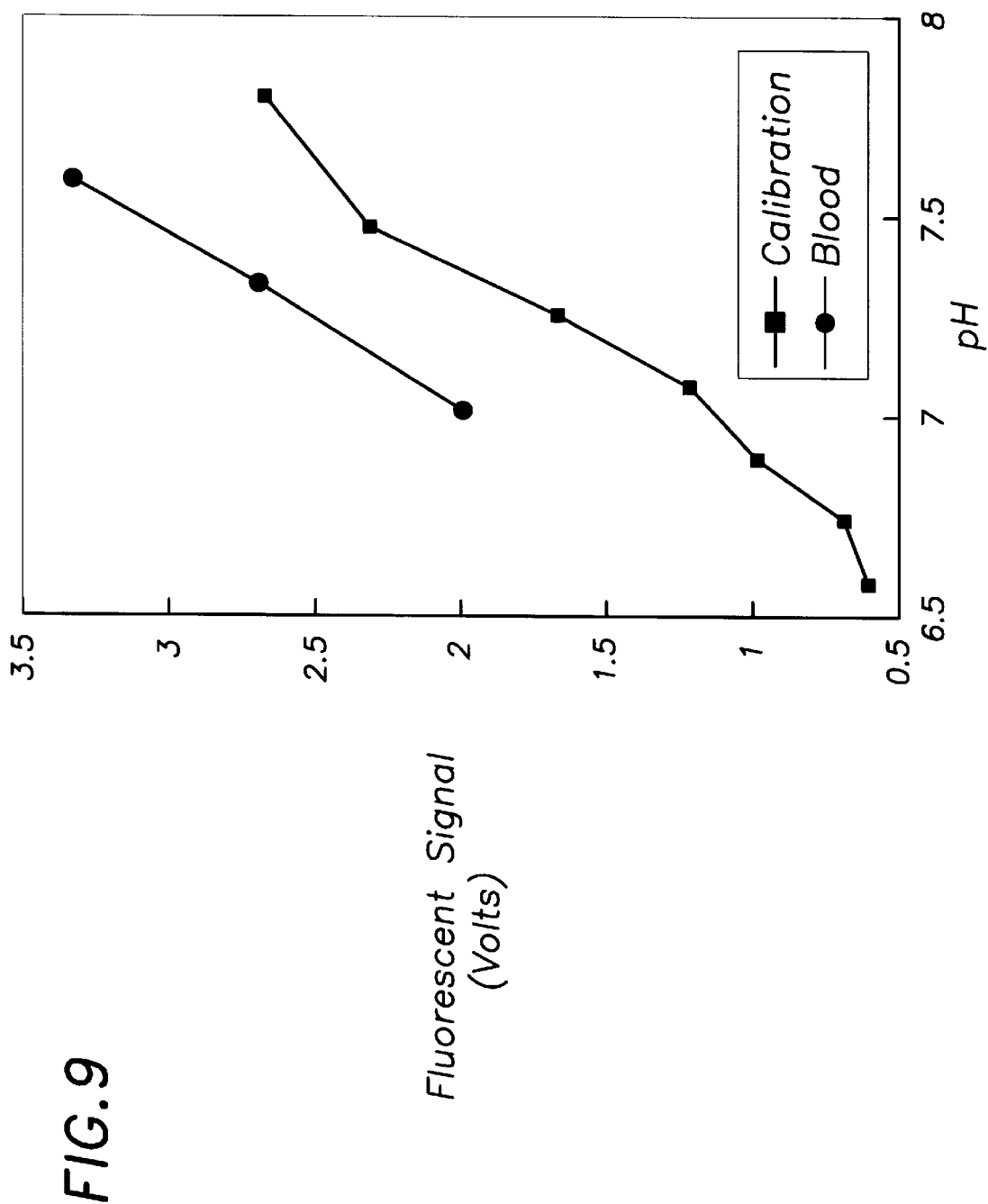
FIG. 9 shows the response to aqueous calibration buffers and blood samples of a pH sensor made without reflecting material, as described in Comparative Example 3.

A comparative control coating solution for a pH sensing layer without added $TiO_2$ was made by dissolving 50 mg of a pH sensitive copolymer composed of N,N-dimethylacrylamide and N-tert-butylacrylamide monomers with a covalently linked 4-acrylamidofluorescein into 1 ml of THF in a manner described by Alder et al. in the World Patent Application WO 95-30148, as previously incorporated by reference. The sensing layer was deposited as a stripe on a MYLAR® polyester film support according to the methods outlined in the Chiron Sensor Application, entitled "Optical Sensor and Method of Operation". After solvent evaporation, the stripes were virtually colorless until wetted by basic aqueous buffer samples whereupon they became faint green. For the data recorded in FIG. 9, both the calibration and blood samples were measured on a Chiron Diagnostics Model 860 blood gas analyzer (available from Chiron Diagnostics Corporation, Norwood, Mass.) prior to the fluorescence measurements with the optical sensor layer. As illustrated by the blood and aqueous calibration curves, there is a significant offset in the optical signals observed.

Example 5

Figure 10:
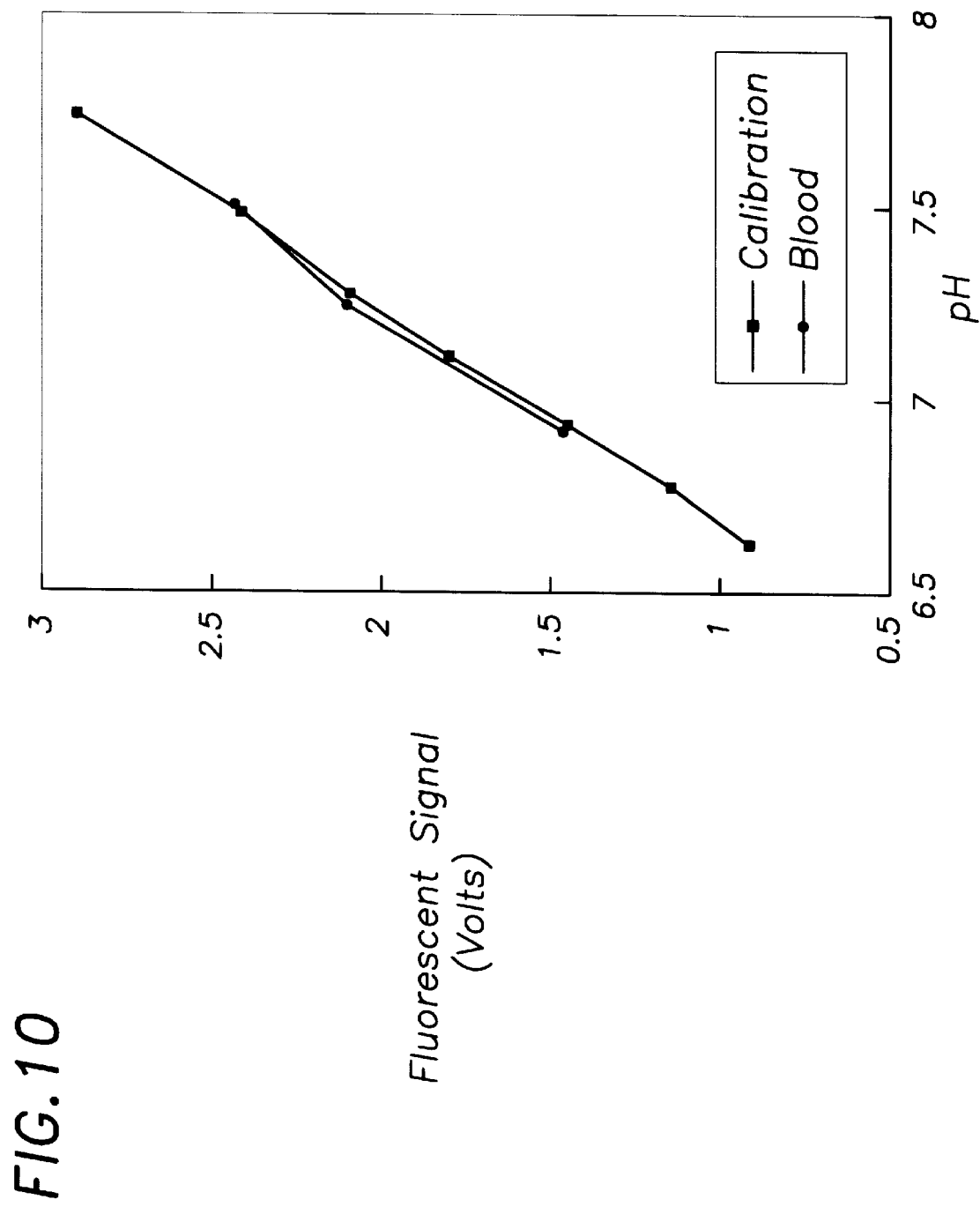
FIG. 10 shows the response to buffers and blood samples of a pH sensor made with a combination of blush polymer and titanium dioxide, as described in Example 5.

To construct a pH detection layer with reflective pigmentation, the solution in Comparative Example 3 was supplemented with 25 mg of $TiO_2$ in the form of Ti-Pure® R-706 dry grade (also available from Du Pont) and 25 mg of the white polymer pigment "TERGOPAK® M2", placed in a capped glass vial with several tungsten carbide beads and milled overnight on a roller apparatus. Deposition steps and measurement methods were the same as described in Comparative Example 3. The curves in FIG. 10 show that there is little difference between the blood samples and the aqueous calibrants when a combination of reflective pigments is used in the sensing layer to diminish the blood scattering effects.

Comparative Example 4

A comparative control coating solution for a $CO_2$ sensing layer without added reflecting material was constructed substantially as set forth in U.S. Pat. No. 5,506,148. A 7% solution (by weight) of ethyl cellulose was prepared by dissolving 7 g in 100 ml of a 7:3 toluene:ethanol mixture. To this solution was added 2 ml of tetrabutylammonium hydroxide and 5 mg of hydroxypyrenetrisulfonic acid (HPTS). The solution was deposited as a sensing layer, as described in Comparative Example 3. After air drying overnight, this produced very faintly green stripes for $CO_2$ sensing. The sensing layer was sensitive to partial pressures of dissolved carbon dioxide and gave increased signals when exposed to blood samples tonometered with equivalent partial pressures of $CO_2$.

Example 6

Figure 11:
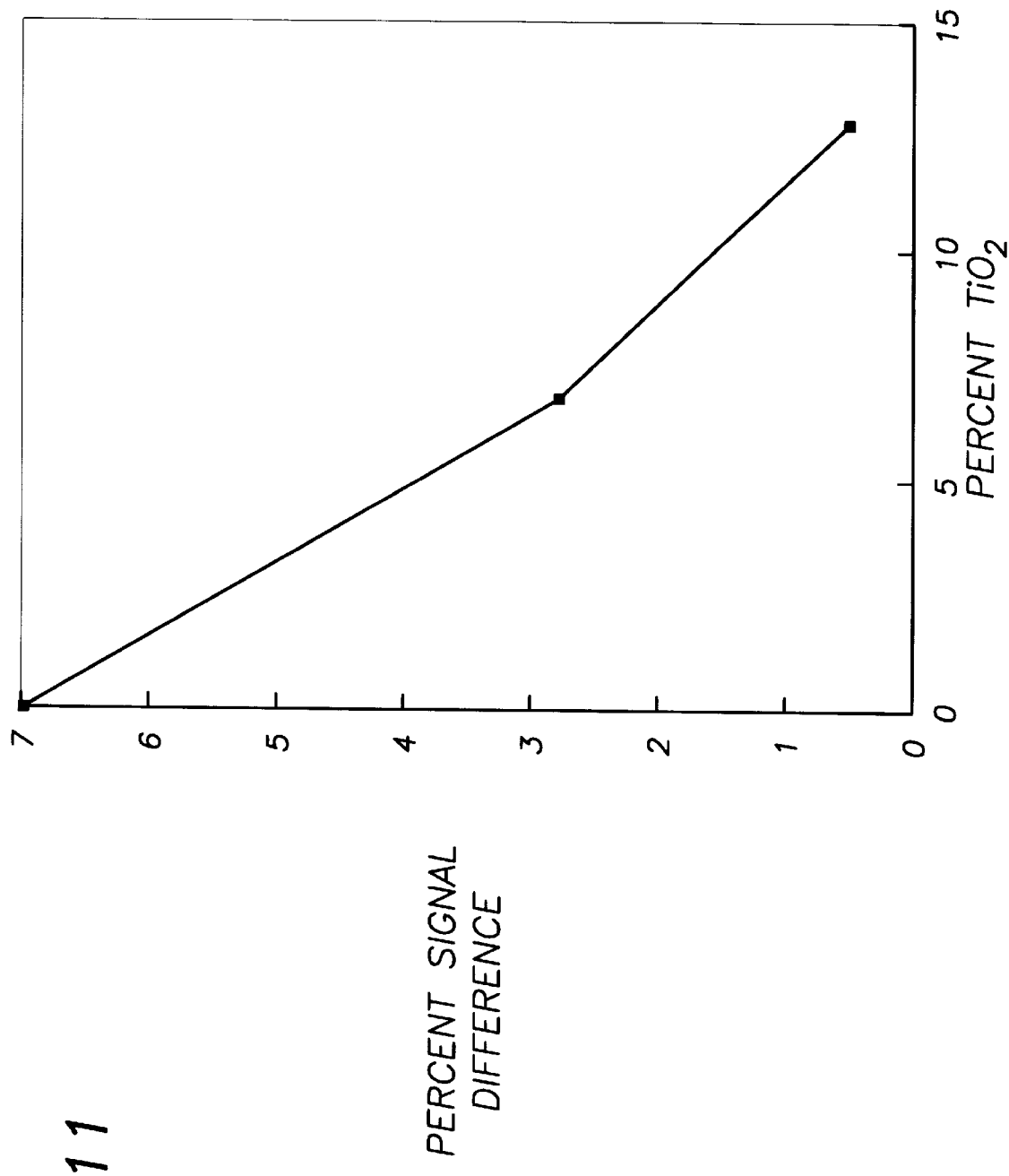
FIG. 11 shows the percentage difference between the luminescent signals observed with blood and aqueous tonometered samples for carbon dioxide sensors, as prepared without reflecting material in Comparative Example 4 and with reflecting material as in Example 6.

A coating solution for a $CO_2$ sensing layer with added reflecting material was constructed from the basic solution described in Comparative Example 4. A 7% solution (by weight) of ethyl cellulose was prepared by dissolving 7 g in 100 ml of a 7:3 toluene:ethanol mixture. To this first solution was added 2 ml of tetrabutylammonium hydroxide and 5 mg of hydroxypyrenetrisulponic acid (HPTS). Coating solutions with reflecting material were prepared by further adding either 80 mg or 160 mg of $TiO_2$ as Ti-Pure® R-706 to 16 ml aliqouts of the second mixture and milling overnight in a capped glass vial containing several tungsten balls. The solution was deposited as a sensing layer as described in Comparative Example 3 and, after air drying overnight, produced sensor layers respectively with 6.6% and 12.5% by weight $TiO_2$. The same tonometered buffer samples and blood samples used in Comparative Example 4 were used for obtaining fluorescent signal values. The percent difference in the signal offsets between blood and aqueous samples is plotted in FIG. 11 for sensors containing 0%, 6.6%, and 12.5% of the reflecting material. The differences between blood and aqueous liquid calibration samples were significantly diminished by the presence and increased levels of the reflective material.

While the invention has been described in detail and with reference to specific and general embodiments thereof, it will be apparent to one skilled in the art that various changes and modifications can be made therein without departing from the spirit and scope thereof.

What is claimed is:

1. An optical sensor comprising a support and a single detection layer, wherein said detection layer
    has a thickness in the range of about 0.2 to 15 µm,
    has an outer surface for contact with an analyte-containing fluid,
    has a response time of less than about 0.7 seconds, and comprises a mixture of:
    (a) a luminescent material wherein the luminescence intensity of said luminescent material varies as the amount of an analyte varies, said luminescent material selected from the group consisting of acridines, fluoresceins, rhodamines, pyrenes, and porphyrins;
    (b) a reflective material having a highly efficient reflectance of the wavelengths of excitation and of emission of said luminescent material, the reflective material representing about 5% to 65% by weight of the detection layer; and
    (c) a polymeric binder.
2. The optical sensor of claim 1, wherein said detection layer has a thickness of from 0.5 to 10 microns.
3. The optical sensor of claim 1, wherein said detection layer has a thickness of from 1 to 8 microns.
4. The optical sensor of claim 1, wherein said reflective material is present in the amount of 10 to 50% of the weight of said detection layer.
5. The optical sensor of claim 1, wherein said reflective material is present in the amount of 30 to 50% of the weight of said detection layer.
6. The optical sensor of claim 1, wherein said reflective material is a pigment.
7. The optical sensor of claim 1, wherein said reflective material is selected from the group consisting of: titanium dioxide, zinc oxide, antimony trioxide, barium sulfate, magnesium oxide, and combinations thereof.
8. The optical sensor of claim 1, wherein said reflective material comprises titanium dioxide.
9. The optical sensor of claim 1, wherein said reflective material comprises a blush polymer pigment.
10. The optical sensor of claim 1, wherein said reflective material comprises a combination of a blush polymer pigment and an inorganic pigment.
11. The optical sensor of claim 1, wherein said detection layer is an outermost layer of said optical sensor adapted for contact with a mixture containing said analyte.
12. The optical sensor of claim 1, wherein said optical sensor consists of said support and said detection layer.
13. The optical sensor of claim 1, wherein said luminescent material is a fluorescent material.
14. The optical sensor of claim 1, wherein said polymeric binder comprises one or more polymers selected from the group consisting of: poly(amides), poly(acrylamides), poly(styrenes), poly(acrylates), poly(alkylacrylates), poly(nitriles), poly(vinyl chlorides), poly(vinyl alcohols), poly(dienes), poly(esters), poly(carbonates), poly(siloxanes), poly(urethanes), poly(olefins), poly(imides), and hetero polymeric combinations thereof; cellulosics and derivatives thereof.
15. The optical sensor of claim 1, wherein said polymeric binder comprises ethyl cellulose.
16. The optical sensor of claim 1, wherein said polymeric binder comprises a copolymer of N,N-dimethylacrylamide and N-tert-butylacrylamide.
17. The optical sensor of claim 1, wherein said luminescent material is a phosphorescent material.
18. The optical sensor of claim 1, wherein said luminescent material is platinum octaethyl porphyrin.
19. The optical sensor of claim 17, wherein said polymeric binder comprises one or more polymers selected from the group consisting of: poly(acrylates), poly(alkylacrylates), poly(styrenes), poly(nitriles), poly(vinyl chlorides), poly(dienes), poly(esters), poly(carbonates), poly(siloxanes), poly(urethanes), and poly(olefins); and hetero polymer combinations thereof.
20. The optical sensor of claim 17, wherein said polymeric binder comprises a copolymer of ethylhexylmethacrylate and methylmethacrylate.
21. The optical sensor of claim 1, wherein said support is substantially transparent to the wavelengths of excitation and of emission of said luminescent material.
22. The optical sensor of claim 21, wherein said support is a flexible plastic film.
23. The optical sensor of claim 1, wherein said analyte is a gas.
24. The optical sensor of claim 23, wherein said gas is selected from the group consisting of: ammonia, carbon dioxide, and oxygen.
25. The optical sensor of claim 1, wherein said analyte is an ionic material.
26. The optical sensor of claim 1, wherein said analyte is a nonionic material.
27. An optical sensor for use in analyzing the amount of oxygen gas in a sample, comprising a support and a single detection layer, wherein said detection layer
    has a thickness in the range of about 0.2 to 15 µm,
    has an outer surface for contact with the oxygen-containing sample, has a response time of less than about 0.7 seconds, and comprises a mixture of:
  (a) platinum octaethyl porphyrin;
  (b) a reflective material having a highly efficient reflectance of the wavelengths of excitation and of emission of the platinum octaethyl porphyrin, wherein said reflective material comprises one or more reflective materials selected from the group consisting of titanium dioxide, zinc oxide, antimony oxide, barium sulfate, magnesium oxide, and blush polymer pigments, the reflective material representing about 5% to 65% by weight of the detection layer; and
  (c) a copolymer of ethylhexylmethacrylate and methylmethacrylate.

28. An optical sensor for use in analyzing the pH of a sample, comprising a single detection layer and a support, wherein said detection layer has a thickness in the range of about 0.2 to 15 µm, has an outer surface for contact with the sample, has a response time of less than about 0.7 seconds, and comprises a mixture of:
  (a) a luminescent material selected from the group consisting of acridines, fluoresceins, rhodamines, and pyrenes;
  (b) a reflective material having a highly efficient reflectance of the wavelengths of excitation and of emission of the platinum octaethyl porphyrin, wherein said reflective material comprises one or more reflective materials selected from the group consisting of titanium dioxide, zinc oxide, antimony oxide, barium sulfate, magnesium oxide, and blush polymer pigments, the reflective material representing about 5% to 65% by weight of the detection layer; and
  (c) ethyl cellulose.

29. An optical sensor for use in analyzing the pH of a sample, comprising a single detection layer and a support, wherein said detection layer has a thickness in the range of about 0.2 to 15 µm, has an outer surface for contact with the sample, has a response time of less than about 0.7 seconds, and comprises a mixture of:
  (a) a luminescent material selected from the group consisting of acridines, fluorseceins, rhodamines, and pyrenes;
  (b) a reflective material having a highly efficient reflectance of the wavelengths of excitation and of emission of said luminescent material, wherein said reflective material is selected from the group consisting of titanium dioxide, zinc oxide, antimony oxide, barium sulfate, magnesium oxide, and blush polymer pigments, the reflective material representing about 5% to 65% by weight of the detection layer; and
  (c) a copolymer of N,N-dimethylacrylamide and N-tert-butylacrylamide.

30. An optical sensor comprising a support and a detection layer comprised of two or more detection regions coated in a pattern on the support, wherein one of the two detection regions has a thickness in the range of about 0.2 to 15 µm, has an outer surface for contact with an analyte-containing fluid, has a response time of less than about 0.7 seconds, and comprises a mixture of:
  (a) a luminescent material selected from the group consisting of acridines, fluoresceins, rhodamines, pyrenes and porphyrins;
  (b) a reflective material having a highly efficient reflectance of the wavelengths of excitation and of emission of said luminescent material, the reflective material representing about 5% to 65% by weight of the detection layer; and
  (c) a polymeric binder.

31. The optical sensor of claim 30, wherein the reflective material comprises one or more reflective materials selected from the group consisting of titanium oxide, zinc oxide, antimony oxide, barium sulfate, magnesium oxide, and blush polymer pigments.

32. The optical sensor of claim 30, wherein the polymeric binder comprises one or more polymers selected from the group consisting of poly(acrylates), poly(alkylacrylates), poly(styrenes), poy(nitriles), poly(vinylchlorides), poly (dienes), poly(esters), poly(carbonates), poly(siloxanes), poly(urethanes), and poly(olefins), and mixtures and copolymers thereof.

33. The optical sensor of claim 30, wherein the detection layer has been cured at a curing temperature above the glass transition temperature of the polymeric binder.

34. The optical sensor of claim 30, wherein each of the detection regions is capable of sensing the concentration of a different analyte.

* * * * *